United States Patent [19]
Rohde

[11] 3,938,658
[45] Feb. 17, 1976

[54] STERILE POUCH

[75] Inventor: William A. Rohde, Arlington Heights, Ill.

[73] Assignee: Tower Products, Inc., Mundelein, Ill.

[22] Filed: Dec. 17, 1973

[21] Appl. No.: 425,306

[52] U.S. Cl. .................................. 206/439; 229/62
[51] Int. Cl.² ........................................ A61D 19/02
[58] Field of Search ........................... 206/438–440; 229/62

[56] References Cited
UNITED STATES PATENTS 3,685,720   8/1972   Brady ................................. 206/438

Primary Examiner—William Price
Assistant Examiner—Douglas B. Farrow
Attorney, Agent, or Firm—Gary, Juettner, Pigott & Cullinan

[57] ABSTRACT

A pouch made from thermoplastic film and particularly suited for sterilizing and storing medical items has an edge defined by a fold of the film. A cap of porous material is wrapped over the folded edge and is sealed thereto along a continuous line to define an enclosed area on both sides of the edge in which the film and cap are unsealed. An opening, such as a slot, is provided in or adjacent to the fold of the film, with the opening being entirely located within the unsealed area and spaced from the seal line. The construction lessens the possibility of open bacteria paths often found in similar prior art pouches.

In the manufacture of the pouch, a web of thermoplastic film is provided with a series of spaced linear openings or slits, a porous sheet material is applied over the openings and the porous material is sealed to the web along a continuous line surrounding the openings. The material is then folded along the line of openings, cut transversely into sections between the ends of the openings, and heat sealed along the sides to form a pouch having an opening at one end and a porous end cap at the other end.

4 Claims, 8 Drawing Figures

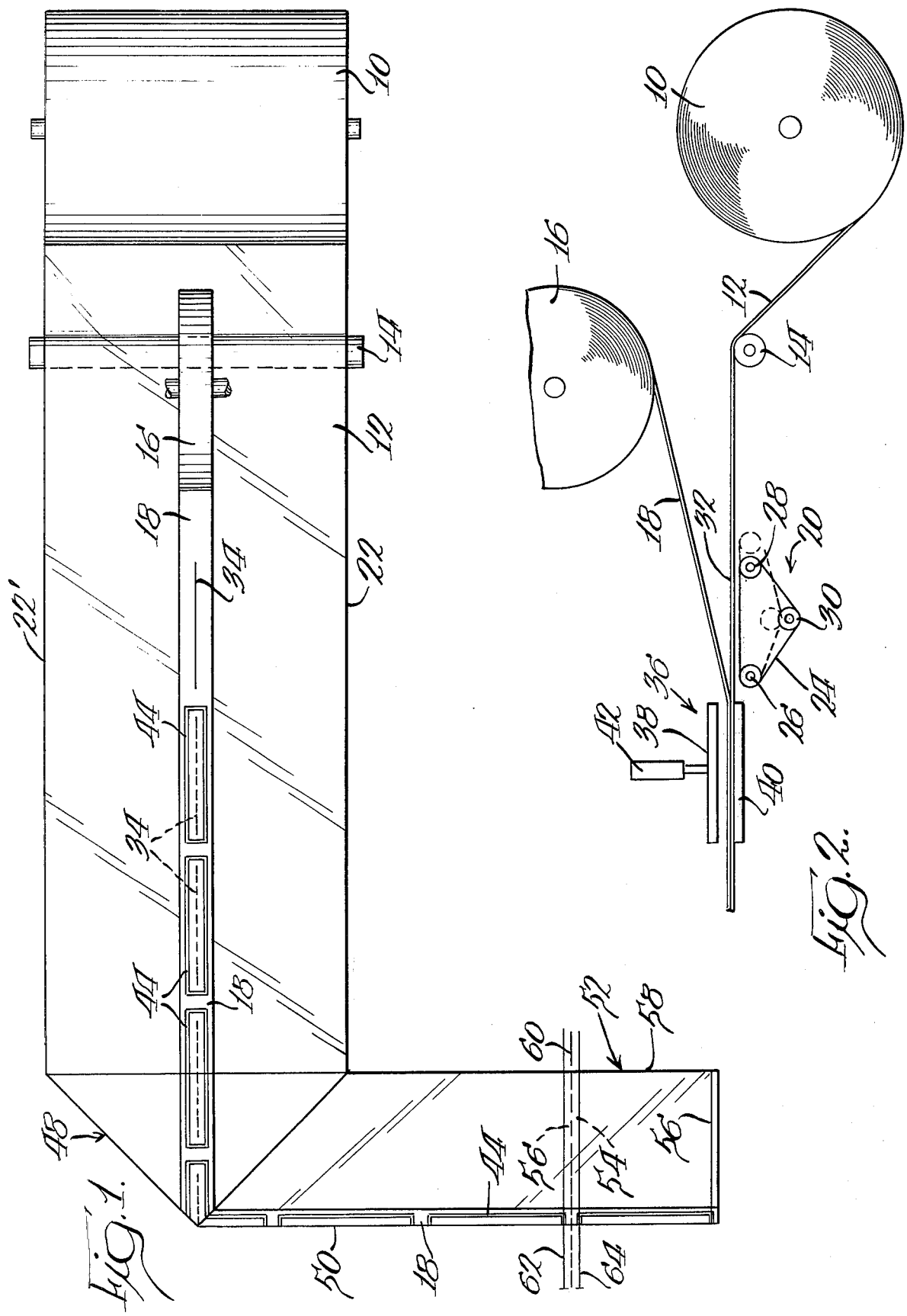

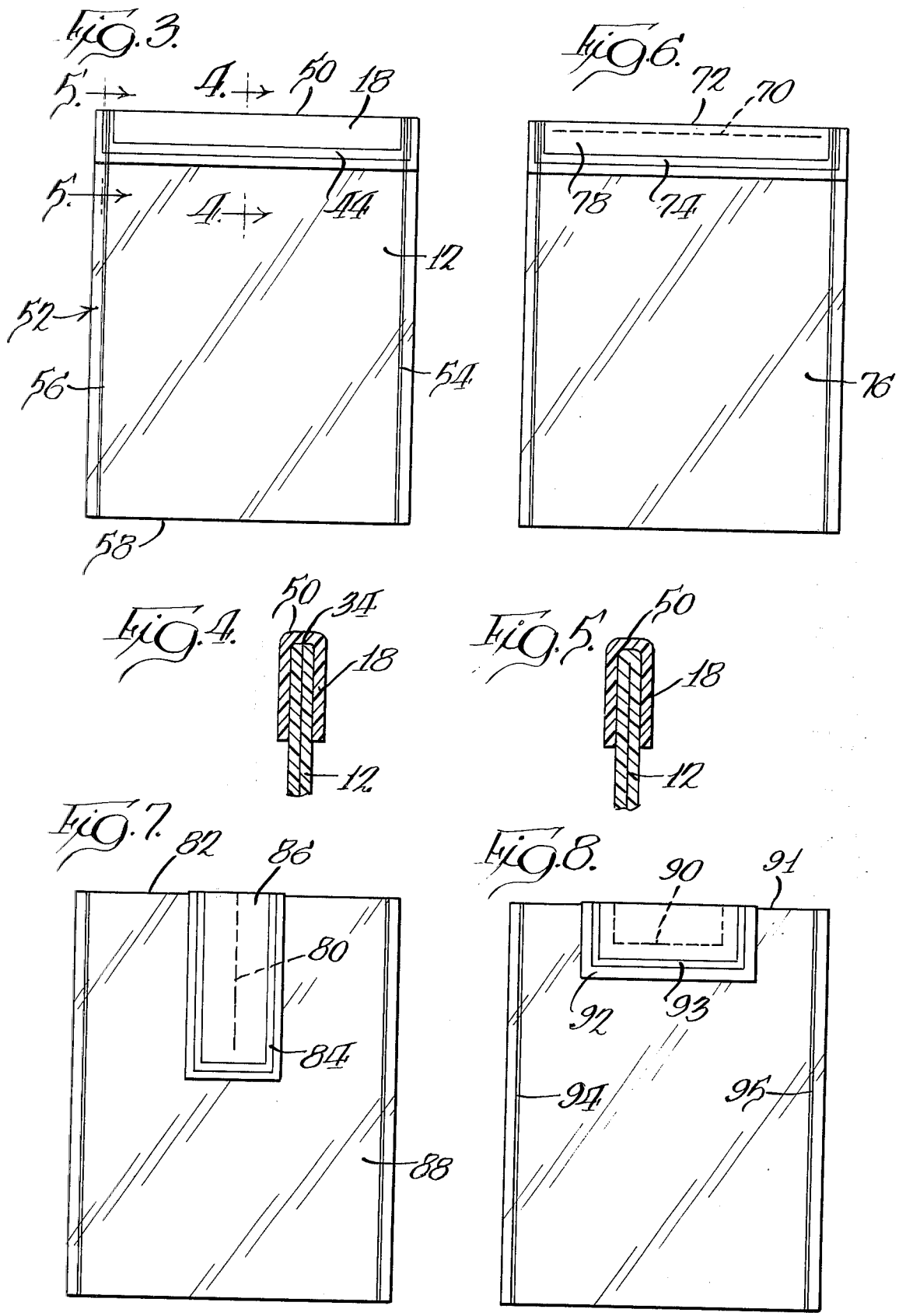

STERILE POUCH

BACKGROUND OF THE INVENTION

It has become commonplace to package and sterilize medical and surgical implements in individual packages, whereby the implements are maintained in a sterile condition until used. A pre-sterile item may be placed into a sterile package to provide a sterile environment, but the most common practice is to sterilize the item within a package or a container. The latter procedure typically involves exposure of the package to an active sterilant such as steam or ethylene oxide.

Since an active sterilant must penetrate into the interior of a package to be effective on the interior of the package and articles therein, it is desirable that the package be sufficiently porous to enable penetration of the sterilant into the package as well as purging of residual gas from the package. At the same time, the porosity must be sufficiently low to prevent penetration of bacteria into the package after sterilization.

Various packages have been proposed to accomplish the above objectives, including packages or pouches composed partially of thermoplastic films and partially of a more porous material, such as paper or a porous polyolefin material. Pouches of this nature are described in the following patents: U.S. Pat. Nos. 3,247,957; 3,338,019; 3,472,369; 3,547,257; 3,627,611 and 3,685,720. In all of the above patents, a window, seam or empty panel of a thermoplastic film pouch is covered by a porous sheet material to facilitate venting of the pouch during the sterilization procedure.

In the formation of pouches from thermoplastic films, it is customary to heat seal plies of film together along lines of seal to provide a composite package. A problem which frequently arises, however, is the inability to obtain a seal of uniform integrity when a plurality of plies of film and porous materials are sealed together simultaneously. This problem becomes acute when one or more of the inner plies terminates within the seal area. The void created at the end of the discontinuous ply must be closed or one or more passageways from the exterior into the interior of the package can be established, thereby destroying the integrity of a sterile condition within the package. This problem frequently arises when a porous sheet is incorporated at one end of the package or pouch.

SUMMARY OF THE INVENTION

The present invention provides a novel pouch construction and method for making the same wherein the pouch has an end cap composed of porous material, while the problem of improper sealing referred to above is largely eliminated. The majority of the pouch is composed of a thermoplastic film which may be easily folded and the edges heat welded together. The access opening into the interior of the pouch is provided by means of a slit or opening in the thermoplastic film, which does not extend to any free edge of the film. The slit is preferably provided in an end fold of the package and is entirely covered by a porous sheet which is heat sealed entirely around the slit.

The pouch is fabricated from lengths of thermoplastic film and porous sheet material. A linear series of slits is provided in the film, and the porous sheet is heat sealed around the periphery of each slit. Thereafter, the film is folded on or adjacent to the line of the slit and is cut into sections between adjacent slits and heat welded along the sides. Preferably, the seal between the porous material and the film is peelable, which enables opening of the pouch by peeling off the porous sheet.

THE DRAWINGS

FIG. 1 is a simplified plan view of the apparatus and materials which are employed in the practice of the present invention;

FIG. 2 is a simplified elevational view of the apparatus shown in FIG. 1;

FIG. 3 is a plan view of the product of the present invention;

FIG. 4 is a sectional view taken along section line 4—4 of FIG. 3;

FIG. 5 is a sectional view taken along section line 5—5 of FIG. 3; and

FIGS. 6, 7 and 8 are plan views of various other embodiments of the product of the present invention.

DESCRIPTION OF THE PREFERRED EMBODIMENTS

The pouch of the present invention is principally composed of a film of thermoplastic or polymeric material, such as a modified or unmodified polyolefin, vinyl polymer, ionomer, polycarbonate, polymethyl methacrylate, fluoro-plastic, polyamide, polyester, or others, as is well known to those skilled in the art of fabricating plastic films. Preferably, the film is of the type which enables superimposed surfaces thereof to be easily heat sealed together by a conventional heated seal bar. In addition, a porous sheet material is employed which may comprise a paper sheet but preferably in the form of a porous polyolefin, such as a spun bonded, non-woven polyolefin sheet sold under the name Tyvek by DuPont Company.

To facilitate understanding of the structure of the pouch, it is convenient to first refer to the process by which the pouch is made, which is shown in a simplified fashion in FIGS. 1 and 2. A roll 10 of the thermoplastic film 12 is provided, which is drawn off the roll as a continuous sheet over suitable rollers 14 or the like. In addition, a narrow roll 16 of porous sheet material 18 is provided, which is drawn off above and parallel to the film 12 so that the film and sheet are coextensive and the porous sheet overlays and may be superimposed on a central lane of the thermoplastic film.

The film 12 passes over an upwardly facing slitting device 20, the function of which is to provide a linear series of spaced slits 34 in the film, said slits running in parallel with the side edges 22 and 22' of the film. The slitting device 20 may comprise a continuous belt 24 stretched around three spaced pulleys 26, 28 and 30, two of which pulleys, 26 and 28, are located in the same plane disposed parallel to the plane of the film 12. An outwardly projecting knife 32 is secured on the belt 24, and means, such as a motor (not shown) is connected to one of the pulleys in order to drive the belt.

The pulleys 26 and 28 are spaced from the film 12 such that the sharp edge of the knife 32 engages and slits the web during its period of travel between said pulleys. The moving knife then passes out of contact with the film as it travels around the lower pulley 30. Preferably, the belt 24 is driven in a direction opposite to the direction of travel of the web, and the knife cuts a linear series of spaced slits 34 in the moving film by virtue of relative timed movement between the knife and the film. The period of engagement between the knife and the film and hence the length of the slit may be adjusted by changing the distance between the upper pulleys 26 and 28, while moving the lower pulley 30 vertically to accommodate the adjustment, an example of which is shown in phantom lines in FIG. 2.

It will be understood that the slitting device 20 is considered as only exemplary of the various available means that may be employed to provide a series of slits or other spaced openings in the film. Other types of cutting and stamping apparatus may be employed to provide the desired series of openings.

After the slitting operation has been completed, the porous strip 18 is brought into intimate contact with the film 12, such that the strip evenly overlays and covers the line of the spaced slits 34. The materials are then passed into a sealing station 36 comprising upper and lower heated platens 38 and 40 having projecting facing sealing surfaces in the shape of rectangles or other enclosed figures. The upper platen 38 is connected to a reciprocating power cylinder 42 which operates in timed relation with the slitter 20. The heated platens are pressed together to seal the porous material 18 to the film 12 along a rectangular line 44 (FIG. 1) around the area of each slit. It will be noted in FIG. 1 that the area enclosed by the continuous seal line 44 is unsealed, and the ends or boundaries of each slit terminate within said area and are spaced from the seal line. It will also be noted that the end of one seal is spaced from the end of an adjacent seal, such that adjacent seals have an unsealed area therebetween.

The sealing station operates continuously, and each downward stroke of the cylinder 42 causes a successive portion of the porous strip 18 to be heat sealed around the sides and ends of a successive slit. Preferably, the surface of the porous strip 18 which faces the film 12 or the facing surface of the film is coated with a hot melt adhesive material or is otherwise treated or composed to form a seal which is peelable at room temperature, which would enable the peeling away of the porous strip and exposure of the slit.

After the porous strip has been applied and sealed, the composite web is passed into a forming station 48 in which the web is folded transversely along its longitudinal center line, which in the embodiment shown, is along a line coincident with the slits 34. The web is folded away from the porous strip 18 such that the strip is disposed around an outside fold or edge 50 of the material, and the slits are coincident with the fold. The resulting web is thus composed of two overlapping halves of the original film.

Following the folding operation, the two ply material is severed between the ends of adjacent spaced seals 44 along a line perpendicular to the folded edge 50 in order to form individual pouches 52. At the same time, the facing side edges adjacent both sides of the severed line are heat welded together along continuous respective lines 54 and 56, which are spaced inwardly from the severed edges and extend entirely from the folded edge 50 to the opposite edge 58. The end 58 is left unsealed, to enable insertion of an article into the pouch at a later time.

The foregoing severing and sealing operation may be accomplished simultaneously by means of a reciprocating knife cut off 60 (FIG. 1) having heated sealing bars 62 and 64 disposed in parallel on both sides of the knife. In this manner, the knife and sealing bars engage the material at the same time and sever the material while forming side seals on adjacent pouches. As shown in FIG. 3, the side seals 54 and 56 may overlap the ends of the rectangular seal 44, since only the facing edges of thermoplastic are being welded together, and these surfaces normally seal easily in comparison with the porous material.

As shown in FIGS. 3–5 the final product comprises a centrally folded section of thermoplastic sheet having a folded edge 50 with a slit 34 therein and having the sides thereof welded together along lines 54 and 56. The product also has a strip of porous material 18 wrapped over the slitted edge 50 and sealed thereto along an enclosed, continuous seal line 44 spaced from the slit or opening. These features are shown in FIGS. 4 and 5 wherein the central portion of the enclosed end of the pouch contains a slit 34 and the edge portions comprise unslitted or continuous folds 50. If the slit 34 were to extend to the edge of the pouch, it would be difficult to provide a good or reliable seal at the corner edges through the multiple thicknesses of material. The free end 58 of the pouch is open, which allows insertion of an article into the pouch, followed by heat welding of the opening at said end.

After the open end 58 has been closed, the pouch and its contents may be sterilized by exposure to an atmosphere of an active sterilant, such as steam or ethylene oxide. The sterilant may easily enter and leave the pouch through the porous end cap 18 and slit 34.

In order to open the pouch and to withdraw the sterile contents, the porous material 18 is peeled away from the body of the pouch, and the contents may be withdrawn through the open slit.

FIGS. 6, 7 and 8 illustrate other embodiments of the product of the present invention. FIG. 6 illustrates a pouch which is identical to that shown in FIG. 3, except that slit 70 is not provided in the edge fold 72; instead, the slit 70 within the thermoplastic sheet is spaced from the fold and is parallel thereto. The slit 70, however, remains within the confines of and is surrounded by a continuous seal 74 between the pouch body 76 and the porous end cap 78. As will be apparent, the pouch of FIG. 6 can be produced by essentially the same process as described in connection with FIGS. 1–5.

FIG. 7 illustrates an embodiment wherein the slit 80 is disposed perpendicular to the folded edge 82 and is surrounded by the seal 84 between the porous cap 86 and the pouch body 88. Again, the cap 86 overlaps the edge 82, and the slit may lie in one of the plies of the pouch or may extend continuously from one ply to another around the edge 82.

FIG. 8 illustrates the possibility of using an opening 90 other than in the form of a slit. In this case, opening 90 is rectangular in shape and extends from one panel of the pouch to the other around the folded edge 91. A porous sheet 92 in the form of an end cap is wrapped over the folded edge 91 and is sealed to the pouch body by a continuous seal line 93. It will also be noted that the side edges of the porous member 92 are spaced inward from the side seals 94 and 95 in the body of the pouch that the seals do not overlap.

The pouches of FIGS. 7 and 8 could, if desired, be produced essentially in the same manner as shown in FIGS. 1 and 2 if the slit 80 or opening 90 were stamped in the film. However, this could be wasteful of the porous sheet material, and it would therefore be preferable to feed incremental segments rather than a continuous strip of the porous sheet 86 or 92 onto the film, in manner known or apparent in the art, to overlie the slit 80 or opening 90, respectively. Otherwise, the process in essence would be the same.

What is claimed is:

1. A pouch comprising a folded flexible thermoplastic film comprising opposed walls with a fold at one edge connecting said walls, a folded porous sheet engaged over said edge and portions of both of said walls, a continuous line of seal between said porous sheet and the underlying portions of said edge and said walls, said line of seal extending over said edge and into both of said opposed walls and defining within said line an enclosed area between said film and said sheet, and an opening in said film within said enclosed area, said opening being located in its entirety within said area and having its boundaries spaced inwardly from said line of seal.

2. The pouch according to claim 1 wherein said opposed walls of said film have side edges extending from said folded edge and wherein said walls are heat welded together along second lines of seal adjacent said side edges, said second lines of seal being spaced outwardly from the boundaries of said opening.

3. The pouch according to claim 2 wherein said continuous line of seal is in its entirety spaced inwardly from said second lines of seal.

4. A pouch comprising a flexible thermoplastic film having two opposed walls sealed together at their side edges and having a fold at one end connecting said walls, a folded porous sheet engaged over said fold and portions of both of said walls, a continuous line of seal between said porous sheet and the underlying portions of said fold and said walls, said line of seal extending over said fold and into both of said walls with the portions of said line adjacent the side edges of said walls extending no further outwardly than the side edge seals between said walls, said line of seal defining within said line an enclosed area between said film and said sheet, and an opening in said film within said enclosed area, said opening being located in its entirety within said area and having its boundaries spaced inwardly from both said line of seal and the side edge seals between said walls.

* * * * *